(12) United States Patent
Reutemann et al.

(10) Patent No.: US 7,518,020 B2
(45) Date of Patent: Apr. 14, 2009

(54) METHOD FOR CONTROLLING THE REACTOR ADMISSION TEMPERATURE DURING THE PRODUCTION OF METHYLAMINE

(75) Inventors: Werner Reutemann, Bobenheim-Roxheim (DE); Rolf Wambsganβ, Landau (DE); Frank Poplow, Ludwigshafen (DE); Theodor Weber, Ludwigshafen (DE); Karl-Heinz Roβ, Grünstadt (DE); Manfred Julius, Limburgerhof (DE)

(73) Assignee: BASF SE, Ludwigshafen (DE)

( * ) Notice: Subject to any disclaimer, the term of this patent is extended or adjusted under 35 U.S.C. 154(b) by 61 days.

(21) Appl. No.: 10/573,185

(22) PCT Filed: Sep. 24, 2004

(86) PCT No.: PCT/EP2004/010765

§ 371 (c)(1),
(2), (4) Date: May 4, 2007

(87) PCT Pub. No.: WO2005/028416

PCT Pub. Date: Mar. 31, 2005

(65) Prior Publication Data

US 2007/0270614 A1    Nov. 22, 2007

(30) Foreign Application Priority Data

Sep. 24, 2003   (DE) .............................. 103 44 283

(51) Int. Cl.
*C07C 209/16* (2006.01)
(52) U.S. Cl. ...................................... 564/479; 564/480
(58) Field of Classification Search .................. None
See application file for complete search history.

(56) References Cited

FOREIGN PATENT DOCUMENTS

JP    A2 60 045 550    3/1985

*Primary Examiner*—Brian J Davis
(74) *Attorney, Agent, or Firm*—Connolly Bove Lodge & Hutz LLP

(57) ABSTRACT

The invention relates to a process for preparing methylamines by gas-phase reaction of methanol and ammonia as starting materials at a pressure in the range from 15 to 30 bar in the presence of heterogeneous catalyst. The starting materials are vaporized in one or more heat exchangers (1, 2, 3), superheated to produce a feed gas stream and subsequently fed into a reactor (4), with the mixing of the starting materials being able to be carried out in the feed stream to one of the heat exchangers (1, 2, 3) or at any desired position in a heat exchanger (1, 2, 3). A product gas stream comprising monomethylamine, dimethylamine and trimethylamine and also reaction by-products is taken off from the reactor (4). To control the reactor inlet temperature of the starting materials to a temperature in the range from 360° C. to 370° C., all or some of the feed gas stream or the product gas stream is passed through an adjustable valve (5) in order to vary the pressure and thus the condensation temperature.

20 Claims, 1 Drawing Sheet

Figure 1:
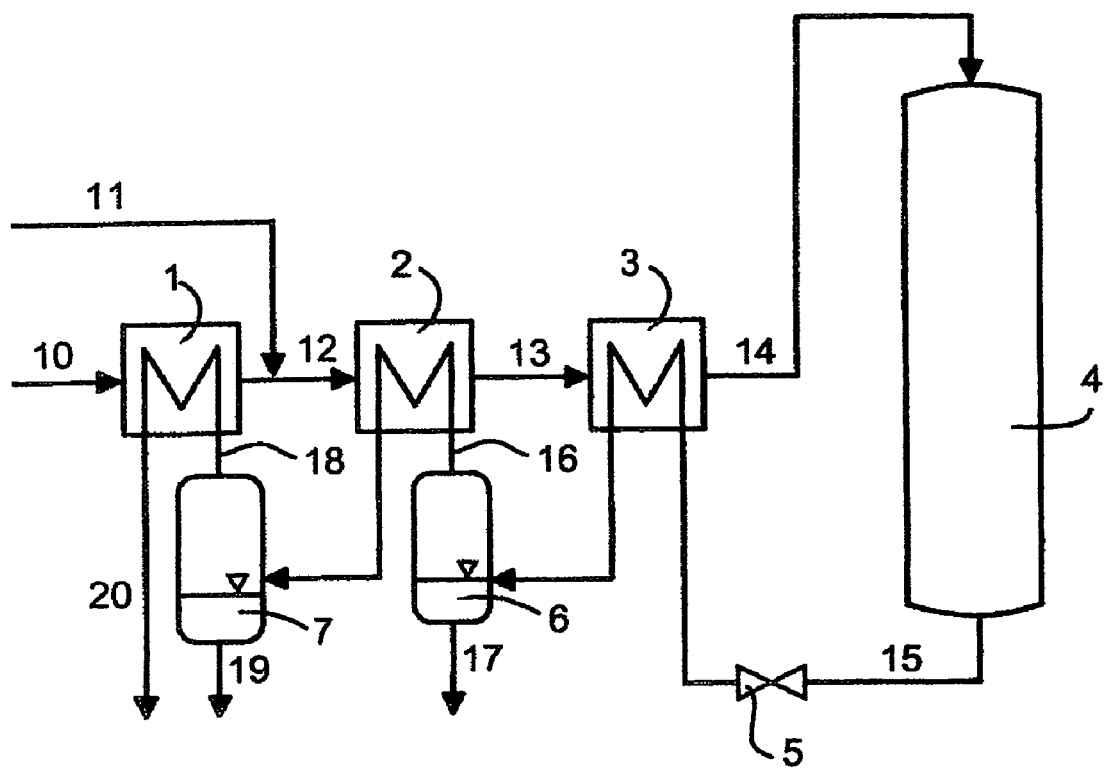

METHOD FOR CONTROLLING THE REACTOR ADMISSION TEMPERATURE DURING THE PRODUCTION OF METHYLAMINE

CROSS REFERENCE TO RELATED APPLICATION

The present application is a National Stage application of PCT/EP 2004/010765, filed Sep. 24, 2004, which claims priority from German Patent Application No. DE 103 44 283.9, filed Sep. 24, 2003.

The present invention relates to a method of regulating the reactor inlet temperature in the preparation of methylamines by gas-phase reaction of methanol and ammonia in the presence of a heterogeneous catalyst. For the reaction to form methylamines to occur, the starting materials have to be preheated before being fed into the reactor.

The product stream obtained in the reaction of methanol and ammonia to form methylamines comprises monomethylamine, dimethylamine and trimethylamine together with water and unreacted ammonia and unreacted methanol. The reaction of methanol and ammonia to form methylamines is exothermic and occurs in the presence of a heterogeneous catalyst. To carry out the reaction, the starting materials methanol and ammonia are preheated before being fed into the reactor.

The reaction of methanol and ammonia to give methylamines forms more trimethylamine than is needed. The excess trimethylamine is added to the reactor feed and reacted in the reactor in an endothermic reaction to produce dimethylamine and monomethylamine. The preheating of the starting materials fed in is carried out in heat exchangers located upstream of the reactor. Preheating can be carried out using the product gas stream obtained in the reaction, as described in JP-A2-60 045 550. For this purpose, the product gas stream is passed through the heat exchangers used for preheating. Owing to the net exothermic nature of the reactions, the temperature increases in the reactor from the reactor inlet to the reactor outlet. Owing to the high temperature at the reactor outlet, no further energy is required for preheating the starting materials in steady-state operation when the product gas stream is used for heating the starting materials.

The temperatures required in the reactor are determined by technical limitations. The reactor inlet temperature has to be high enough for the reaction to start immediately in the reactor. Furthermore, the maximum temperature in the reactor must not be too high, since otherwise decomposition of the methylamines to form gaseous and solid degradation products takes place to an increased extent. However, the maximum temperature in the reactor has to be high enough for most of the methanol to be reacted and for the thermal equilibrium to be reached.

In methods used at present for preheating the starting materials, fluctuations in the reactor inlet temperature can occur as a result of temperature fluctuations in the surroundings or due to different amounts of trimethylamine to be recycled. The fluctuations in the reactor inlet temperature also lead to fluctuations in the maximum temperature in the reactor. In the most unfavorable case, the maximum reactor temperature is so high that the methylamines decompose again.

It is an object of the present invention to provide a process for preparing methylamines from methanol and ammonia by gas-phase reaction, in which the reactor inlet temperature and/or outlet temperature are/is controlled within a narrow range. Furthermore, virtually no energy should have to be introduced from the outside for preheating and superheating the starting materials in steady-state operation of the process for preparing methylamines.

We have found that this object is achieved by the reactor inlet temperature and/or outlet temperature in the process for preparing methylamines being controlled by passing the feed gas stream through an adjustable valve before entering the reactor or passing the product gas stream through an adjustable valve after leaving the reactor.

To prepare methylamines from methanol and ammonia as starting materials, the starting materials are firstly vaporized and superheated in one or more heat exchangers. The starting materials which have in this way been heated to a temperature in the range from 350° C. to 450° C., preferably in the range from 350° C. to 400° C. and particularly preferably in the range from 360° C. to 370° C., are fed at this temperature as reactor inlet temperature into a reactor.

Apart from methanol and ammonia, the reaction by-products formed in the reaction are also fed into the reactor. For this purpose, the reaction products are separated off from the product gas stream in an after-treatment after the reaction.

In the reactor, the starting materials are converted into monomethylamine, dimethylamine and trimethylamine at a pressure in the range from 15 to 30 bar in the presence of a heterogeneous catalyst. The reaction to form methylamines from methanol and ammonia is exothermic, so that the temperature in the reactor increases. A product gas stream comprising monomethylamine, dimethylamine and trimethylamine together with unreacted methanol and unreacted ammonia and also water produced as by-product in the reaction and further by-products such as carbon monoxide and carbon dioxide is taken off from the reactor.

Owing to the exothermic reaction, the temperature increases from the reactor inlet to the reactor outlet. To prevent the temperature in the reactor from exceeding 450° C., heat of reaction can be removed by cooling the reactor.

In the formation of the methylamines, more trimethylamine than can be utilized is normally produced. The unutilized trimethylamine is fed back into the reaction with the feed stream. The conversion of trimethylamine into dimethylamine is endothermic. This consumes heat of reaction liberated in the exothermic reaction of ammonia and methanol to form methylamines. For this reason, the reactor can also be operated adiabatically.

The heat required for starting up the reaction can be supplied by additional heating of the starting materials.

In the process of the present invention for preparing methylamines, the gas stream is passed through a valve after vaporization and superheating of the starting materials. The pressure of the gas stream and thus the condensation temperature downstream of the reactor can be varied by means of the valve. The valve can for this purpose be installed upstream or downstream of the reactor.

To pass heat to the starting materials, the product gas stream is preferably conveyed in countercurrent to the feedstream in the heat exchanger or exchangers. During the transfer of heat to heat up the starting materials, the product stream is at least partly condensed in the heat exchangers. To avoid erosion caused by entrained droplets of condensate, a condensate precipitator can be installed downstream of each of the individual heat exchangers.

A reduction in the cross section effected in the valve and the associated decrease in pressure of the gas stream downstream of the valve results in a decrease in the condensation temperature of the product gas stream. Owing to the lower condensation temperature of the product gas stream, the feedstream is heated to a lesser degree. As a result, the reactor inlet temperature decreases. If, on the other hand, the valve is opened further and the pressure downstream of the valve therefore increases, the condensation temperature of the product gas stream also increases. In this way, the reactor inlet temperature of the starting materials is increased.

If the heat transferred from the product gas stream is not sufficient to preheat the starting materials, steam can be added to the product gas stream, for example in the stream flowing into one of the heat exchangers. The additional steam increases the quantity of heat transferred to the starting materials.

Apart from the addition of steam, there is also the possibility of, when the quantity of heat transferred from the product gas stream is too high, taking off part of the product gas stream before it enters the heat exchangers. In this case, a substream of the product gas stream can be branched off at any point known to those skilled in the art between the heat exchangers or in the heat exchanger. The amount of product gas substream branched off is preferably controlled by means of a valve.

A further possible way of controlling the temperature in accordance with the solution provided by the process of the present invention for preparing methylamine is to vary the point at which the methanol stream is mixed into the ammonia-containing feed stream. The methanol can be mixed in at any point known to those skilled in the art between the individual heat exchangers or at any point known to those skilled in the art in a heat exchanger. However, the methanol is preferably added between two heat exchangers or downstream of the last heat exchanger. In addition, the feed stream comprising ammonia and reaction by-products can be preheated before the methanol is mixed in.

The valve for varying the pressure of the product gas stream is preferably configured so that the pressure at the valve inlet is from 0 to 5 bar higher than at the valve outlet. Furthermore, the valve can preferably be adjusted in a stepless fashion.

A valve for the purposes of the present invention is a valve in which a shutoff body, for example a plate, a cone, a piston or a sphere, opens a cylindrical annular cross section parallel to the flow direction by means of a lifting movement, a slider in which the shutoff body opens a flow cross section perpendicular to the flow direction by means of parallel or wedge-like surfaces or a stopcock or rotary slider in which the shutoff body rotates about its axis perpendicular to the flow direction and thereby opens a flow cross section. Apart from the construction types mentioned, a valve can also be any further construction known to those skilled in the art for the shutting off tube cross sections in which the tube cross section can be varied.

As heat exchangers for preheating the starting materials, it is possible to use all heat exchanger types known to those skilled in the art. Suitable heat exchangers are, for example, shell-and-tube heat exchangers, coil heat exchangers or plate heat exchangers. However, preference is given to using shell-and-tube heat exchangers. The heat exchangers used can be operated in cocurrent, countercurrent or cross-current. Furthermore, any combination of cross-current, countercurrent and cocurrent known to those skilled in the art is possible. Thus, for example, when a plurality of heat exchangers is used, at least one heat exchanger can be operated in cocurrent while the remaining heat exchangers operate in countercurrent. The preferred mode of operation of the heat exchangers for heating the starting materials is countercurrent.

To be able to control the reactor inlet temperature, measurements are taken at various points on the plant for preparing methylamines. Thus, for example, the flow of the ammonia-containing feed stream and the flow of the methanol stream can be measured prior to mixing the methanol into the ammonia-containing feed stream. Furthermore, when the methanol is introduced into the ammonia-containing feed stream at various positions, the flow of the individual methanol substreams can be measured. When the product stream is divided into a plurality of substreams, a flow measurement can be made in any substream. Finally, the amount of additional steam for heating the starting materials can be measured by means of a flow measurement.

To control the reactor inlet temperature, it is also necessary to measure the reactor inlet temperature. Apart from the reactor inlet temperature, it is also possible to measure the temperature of the ammonia-containing feed stream, the temperature of the methanol and the temperature at the reactor outlet. Finally, the pressure difference between the stream flowing into the first heat exchanger and the product stream leaving the first heat exchanger for preheating the starting materials can advantageously be measured.

The liquid product streams obtained in the condensate separators and the product stream leaving the first heat exchanger are preferably passed to a further treatment to separate off the methylamines.

The invention is illustrated below with the aid of a drawing.

FIG. 1 shows a flow diagram of a process designed according to the present invention for preparing methylamines.

In the process depicted in FIG. 1 for preparing methylamine, an ammonia-containing feed stream forms the feed 10 to a first preheater 1. The feed 10 can comprise ammonia together with by-products obtained in the preparation of methylamines and also excess methylamines. In the process depicted in FIG. 1, the feed 10 is preheated in the first preheater 1, subsequently mixed with a methanol stream 11 and fed as feed stream 12 into a second preheater 2. In the following, the substances present in the feed stream 12 in the second preheater 2 are referred to as starting materials. In FIG. 1, the starting materials which have been heated further in the second preheater 2 are conveyed as a feed stream 13 to a superheater 3. In the superheater 3, the starting materials are superheated to the reactor inlet temperature. The starting materials which have been heated in this way to the reactor inlet temperature are fed as a reactor feed 14 to a reactor 4. In the reactor 4, methanol and ammonia react exothermically to form monomethylamine, dimethylamine and trimethylamine. In addition, the trimetbylamine which is formed in large amounts in the reaction but is required in only small amounts and is recirculated to the reactor via the feed stream is converted into dimethylamine and monomethylamine in an endothermic reaction. However, the net effect of all the reactions occurring in the reactor 4 is exothermic. For this reason, the temperature increases along the reactor 4. The reaction products are taken off via a reactor outlet 15. The product gas stream taken off via the reactor outlet 15 is passed through a valve 5 by means of which the pressure upstream of the valve 5 can be varied. Apart from the embodiment shown in FIG. 1, in which the valve 5 is located downstream of the reactor 4, the valve 5 can also be located upstream of the reactor 4. A reduction in the pressure leads to the vaporization temperature of the feed gas stream decreasing, while an increase in the pressure leads to the vaporization temperature of the feed gas stream increasing.

In the embodiment shown in FIG. 1, the product gas stream is conveyed in countercurrent through the superheater 3 and the second preheater 2 and also the first preheater 1. To avoid erosion in the first preheater 1, second preheater 2 and superheater 3, a first droplet precipitator 6 is located between the superheater 3 and the second preheater 2 and a second droplet precipitator 7 is installed between the second preheater 2 and the first preheater 1. In the droplet precipitators 6, 7, the condensate formed in the superheater 3 and the second preheater 2 is separated from the product gas stream. The condensate obtained in the first droplet precipitator 6 is passed via a condensate outlet 17 to a product work-up step not shown in FIG. 1. In an analogous fashion, the condensate obtained in the second droplet precipator 7 is passed via a condensate outlet 19 to the product work-up. The product stream leaving the first preheater 1 is likewise conveyed via a product outlet 20 to the product work-up. In the product work-up, monomethylamine, dimethylamine and trimethylamine are separated off from the product stream. Since the reaction to produce dimethylamine forms far more trimethylamine than is required commercially, the excess trimethylamine is recirculated to the reaction via the feed 10. Correspondingly, excess monomethylamine is fed back into the reaction via the feed 10.

Apart from adjusting the reactor inlet temperature by adjusting the pressure via the valve 5, it is also possible to control the reactor inlet temperature by introducing steam into the product gas stream downstream of the valve 5, into the heating medium stream 16, 18 into the second preheater 2 or into the heating medium stream 18 into the first preheater 1. Apart from the introduction of steam into the heating medium stream 16, 18 into one of the heat exchangers 1, 2, 3, the steam can also be introduced directly into the heating medium in one of the heat exchangers 1, 2, 3.

Apart from the methanol feed stream 11 between the first preheater 1 and the second preheater 2, the methanol can also be introduced into the feed 10 to the first preheater 1 or into the feed stream 13 into the superheater 3 or directly into the reactor feed 14. Apart from introduction of all of the methanol into the feed 10 to the first preheater 1, the feed stream 12 into the second preheater 2, the feed stream 13 into the superheater 3 or the reactor feed 14, the methanol feed stream 11 can also be divided into individual substreams. In this case, the substreams can be mixed into the feed streams at various positions.

Apart from the embodiment shown in FIG. 1 having a first preheater 1, a second preheater 2 and a superheater 3, it is also possible to use only one heat exchanger for vaporization and superheating, one heat exchanger for vaporization and one heat exchanger for superheating. Any other number of heat exchangers for vaporization and superheating of the feed stream is also conceivable.

Apart from the operation of the heat exchangers 1, 2, 3 in countercurrent as shown in FIG. 1, operation in cocurrent or in cross-current is also conceivable, likewise any known combination of countercurrent, cocurrent or cross-current.

Particularly when using only one heat exchanger for vaporization and superheating of the feed stream, the methanol feed stream 11 should be able to be introduced at any position on the heat exchanger.

Controlling of the pressure of the product gas stream by means of the valve 5, the position of the methanol inflow 11 and the optional addition of steam to the product stream for heating the starting materials enables the reactor inlet temperature to be controlled to a temperature in the range from 360° C. to 370° C. Controlling of the reactor inlet temperature to a temperature in the range from 360° C. to 370° C. ensures that the temperature in the reactor does not exceed 450° C. The increase in temperature in the reactor 4 is produced by the heat liberated in the exothermic reaction to form methylamines. However, part of the heat is required for the endothermic reaction of trimethylamine. To keep the reactor temperature in the range from 360° C. to 450° C., the reactor can be operated adiabatically or heat of reaction can be removed by cooling the reactor 4.

The activation energy necessary for the reaction is preferably supplied by means of electric heating at the beginning of the reaction.

LIST OF REFERENCE NUMERALS

1 First preheater
2 Second preheater
3 Superheater
4 Reactor
5 Valve
6 First droplet precipitator
7 Second droplet precipitator
10 Feed
11 Methanol feed stream
12 Feed stream into the second preheater 2
13 Feed stream into the superheater 3
14 Reactor feed
15 Reactor outlet
16 Heating medium stream into the second preheater 2
17 Condensate outlet
18 Heating medium stream into the first preheater 1
19 Condensate outlet
20 Product outlet

We claim:

1. A process for preparing methylamines comprising gas-phase reaction of methanol and ammonia as starting materials at a pressure in the range from 15 to 30 bar in the presence of a heterogeneous catalyst, which further comprises vaporizing the starting materials in one or more heat exchangers, superheating them to form a feed gas stream and subsequently feeding this into a reactor, with the starting materials either being mixed in the feed stream to one of the heat exchangers or at any other position on the heat exchanger, and taking off a product gas stream comprising monomethylamine, dimethylamine and trimethylamine and also reaction by-products from the reactor, wherein the reactor inlet temperature of the starting materials is controlled to a temperature in the range from 360° C. to 370° C. by passing part or all of the feed gas stream or product gas stream through an adjustable valve in order to vary the pressure.

2. A process as claimed in claim 1, wherein the valve can be adjusted steplessly.

3. A process as claimed in claim 1, wherein the valve is installed upstream or downstream of the reactor.

4. A process as claimed in claim 1, wherein the product gas stream is used for vaporizing and superheating the starting materials, resulting in partial condensation of the product gas stream.

5. A process as claimed in claim 1, wherein a substream of the product gas stream is used for vaporizing and superheating the starting materials.

6. A process as claimed in claim 1, wherein the reaction by-products formed in the reaction are separated off from the product gas stream and fed back into the reactor.

7. A process as claimed in claim 6, wherein the ammonia and the reaction by-products fed back into the reactor are preheated before the methanol is added.

8. A process as claimed in claim 1, wherein steam is added to the product gas stream to preheat and superheat the starting materials.

9. A process as claimed in claim 1, wherein the reactor is operated adiabatically.

10. A process as claimed in claim 1, wherein heat of reaction is removed by cooling the reactor.

11. A process as claimed in claim 1, wherein, when a plurality of heat exchangers is used for vaporization and superheating of the starting materials, a droplet precipitator for separating condensate from the product gas stream is installed downstream of each heat exchanger.

12. A process as claimed in claim 1, wherein the pressure at the inlet of the valve is from 0 to 5 bar higher than at the outlet of the valve.

13. A process as claimed in claim 1, wherein the starting materials are heated up electrically to start the reaction.

14. A process as claimed in claim 1, wherein vaporization and superheating of the starting materials is carried out in countercurrent.

15. A process as claimed in claim 1, wherein vaporization and superheating of the starting materials is carried out in cocurrent.

16. A process as claimed in claim 1, wherein, when a plurality of heat exchangers is used for vaporization and superheating of the starting materials, at least one heat exchanger operates in cocurrent and at least one heat exchanger operates in countercurrent.

17. A process as claimed in claim 2 wherein the valve is installed upstream or downstream of the reactor.

18. A process as claimed in claim 2 wherein the product gas stream is used for vaporizing and superheating the starting materials, resulting in partial condensation of the product gas stream.

19. A process as claimed in claim 3 wherein the product gas stream is used for vaporizing and superheating the starting materials, resulting in partial condensation of the product gas stream.

20. A process as claimed in claim 2 wherein a substream of the product gas stream is used for vaporizing and superheating the starting materials.

* * * * *